United States Patent [19]

Karanewsky

[11] 4,448,772
[45] May 15, 1984

[54] PHOSPHINYLMETHYLAMINOCARBONYL IMINO ACID COMPOUNDS USEFUL FOR TREATING HYPERTENSION

[75] Inventor: Donald S. Karanewsky, Princeton Junction, N.J.

[73] Assignee: E. R. Squibb & Sons, Inc., Princeton, N.J.

[21] Appl. No.: 371,033

[22] Filed: Apr. 22, 1982

[51] Int. Cl.³ .................. A61K 31/675; C07F 9/65
[52] U.S. Cl. ................................ 424/200; 546/22; 546/23; 548/112; 548/119; 548/409; 548/413; 548/414
[58] Field of Search ............... 548/409, 413, 414, 112, 548/119; 546/22, 23; 424/200

[56] References Cited

U.S. PATENT DOCUMENTS

| | | | |
|---|---|---|---|
| 4,105,776 | 8/1978 | Ondetti et al. | 424/274 |
| 4,129,566 | 12/1978 | Ondetti et al. | 546/326 |
| 4,151,172 | 4/1979 | Ondetti et al. | 548/413 |
| 4,154,935 | 5/1979 | Ondetti et al. | 546/189 |
| 4,168,267 | 9/1979 | Petrillo | 548/413 |
| 4,192,878 | 3/1980 | Ondetti | 424/370 |
| 4,217,359 | 8/1980 | Krapcho | 424/274 |
| 4,234,489 | 11/1980 | Ondetti et al. | 424/274 X |
| 4,303,583 | 12/1981 | Kim et al. | 424/200 X |
| 4,311,697 | 1/1982 | Krapcho | 424/240 |
| 4,316,896 | 2/1982 | Thorsett et al. | 548/414 X |
| 4,316,905 | 2/1982 | Krapcho | 424/274 |
| 4,316,906 | 2/1982 | Ondetti et al. | 424/274 |
| 4,337,201 | 6/1982 | Petrillo | 548/413 |
| 4,374,131 | 2/1983 | Petrillo, Jr. | 548/413 X |
| 4,379,146 | 4/1983 | Greenlee et al. | 424/177 |
| 4,381,297 | 4/1983 | Karanewsky et al. | 424/200 |

FOREIGN PATENT DOCUMENTS

| | | |
|---|---|---|
| 868532 | 10/1978 | Belgium . |
| 9183 | 4/1980 | European Pat. Off. . |
| 18539 | 11/1980 | European Pat. Off. . |
| 2027025 | 2/1980 | United Kingdom . |

OTHER PUBLICATIONS

Tanabe, Derwent 06738 D/105-Abstract Japanese Applic. No. 5151-555.

*Primary Examiner*—Donald G. Daus
*Assistant Examiner*—Diana G. Rivers
*Attorney, Agent, or Firm*—Lawrence S. Levinson; Stephen B. Davis

[57] ABSTRACT

This invention is directed to phosphinylmethylaminocarbonyl imino acid compounds of the formula

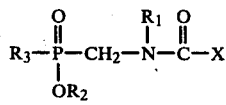

wherein X represents various unsubstituted or substituted imino acids or esters.

15 Claims, No Drawings

PHOSPHINYLMETHYLAMINOCARBONYL IMINO ACID COMPOUNDS USEFUL FOR TREATING HYPERTENSION

BACKGROUND OF THE INVENTION

Petrillo in U.S. Pat. No. 4,168,267 discloses that various phosphinylalkanoyl substituted prolines are useful as hypotensive agents due to their ability to inhibit the angiotensin converting enzyme.

Ondetti, et al. in U.S. Pat. No. 4,151,172 discloses that various phosphonoacyl prolines are useful as hypotensive agents due to their ability to inhibit the angiotensin converting enzyme.

Mercaptoacyl derivatives of proline and substituted prolines are known to be useful hypotensive agents due to their angiotensin converting enzyme inhibition activity. Ondetti, et al. in U.S. Pat. No. 4,105,776 disclose such compounds wherein the proline ring is unsubstituted or substituted by an alkyl or hydroxy group. Ondetti, et al. in U.S. Pat. No. 4,154,935 disclose such compounds wherein the proline ring is substituted with one or more halogens. Ondetti, et al. in U.S. Pat. No. 4,316,906 disclose such compounds wherein the proline ring is substituted by various ethers and thioethers. Krapcho in U.S. Pat. No. 4,217,359 disclose such compounds wherein the proline ring has a carbamoyloxy substituent. Krapcho in U.S. Pat. No. 4,311,697 discloses compounds wherein the proline ring has a di-ether, diethioether, ketal or thioketal substituent in the 4-position. Krapcho in U.S. Pat. No. 4,316,905 discloses such compounds wherein the proline ring has a cycloalkyl, phenyl, or phenyl-lower alkylene substituent. Ondetti, et al. in U.S. Pat. No. 4,234,489 disclose such compounds wherein the proline has a keto substituent in the 5-position. Krapcho, et al. in U.S. Ser. No. 162,341 filed June 23, 1980, now U.S. Pat. No. 4,310,461 disclose such compounds wherein the proline has an imido, amido, or amino substituent in the 4-position. Iwao, et al. in U.K. patent application No. 2,027,025 disclose such compounds wherein the proline has an aromatic substituent in the 5-position.

Mercaptoacyl derivatives of 3,4-dehydroproline are disclosed as angiotensin converting enzyme inhibitors by Ondetti in U.S. Pat. No. 4,129,566. Mercaptoacyl serivatives of thiazolidinecarboxylic acid and substituted thiazolidinecarboxylic acid are disclosed as angiotensin converting enzyme inhibitors by Ondetti in U.S. Pat. No. 4,192,878 and by Yoshitomo Pharmaceutical Ind. in Belgian Pat. No. 868,532.

Tanabe in European patent application No. 18,549 disclose angiotensin converting enzyme inhibitors having a carboxyethylcarbamoyl group attached to the N-atom of tetrahydroisoquinoline carboxylic acid and this same sidechain coupled to the N-atom of proline in Japanese Application No. 5151-555.

Thorsett, et al. in European patent application Ser. No. 9,183 disclose phosphoryl derivatives of aminoacids including proline. These compounds are disclosed as being hypotensive agents due to their angiotensin converting enzyme inhibition activity.

SUMMARY OF THE INVENTION

This invention is directed to new phosphinylmethylaminocarbonyl imino acids of formula I and salts thereof

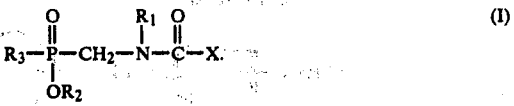

X is an imino acid of the formula

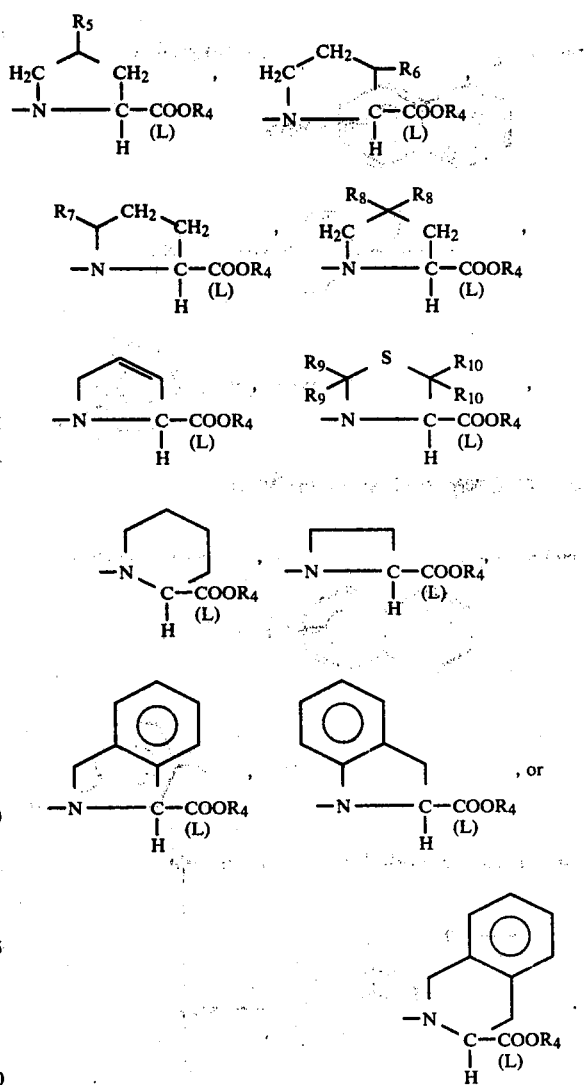

$R_5$ is hydrogen, lower alkyl, halogen, keto, hydroxy,

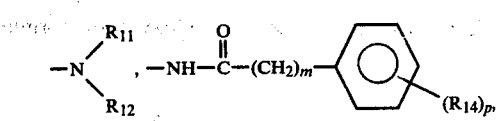

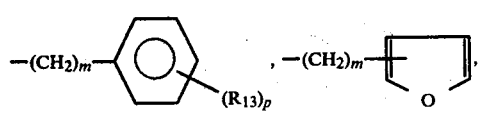

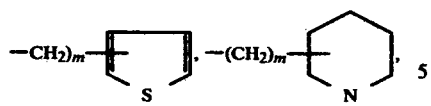

a 1- or 2-naphthyl of the formula

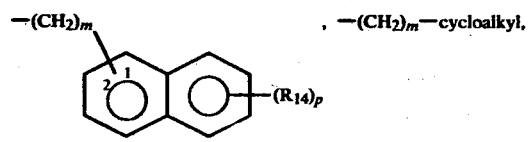

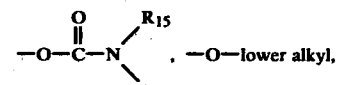

a 1- or 2-naphthyloxy of the formula

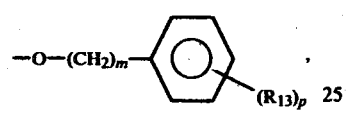

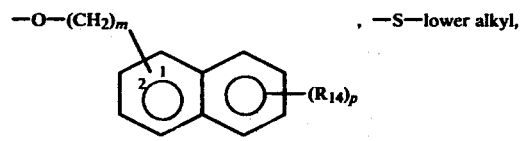

or a 1- or 2-naphthylthio of the formula

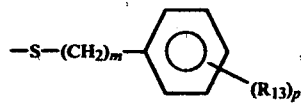

$R_6$ is keto, halogen,

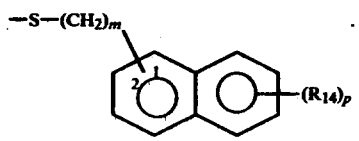

—O—lower alkyl, a 1- or 2-naphthyloxy of the formula

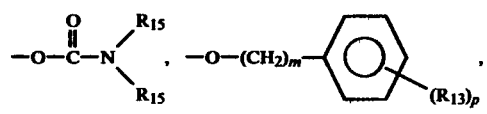

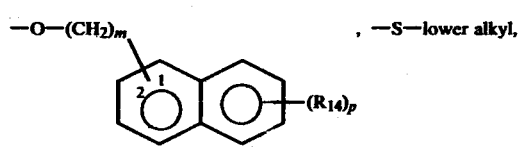

or a 1- or 2-naphthylthio of the formula

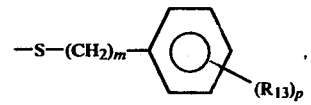

$R_7$ is keto or

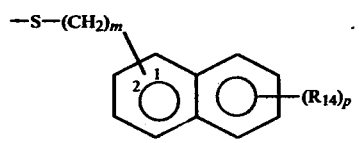

$R_7$ is keto or

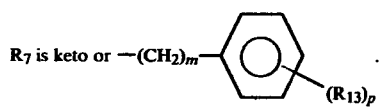

$R_8$ is halogen or —Y—$R_{16}$.

$R_9$, $R_9'$, $R_{10}$ and $R_{10}'$ are independently selected from hydrogen and lower alkyl or $R_9'$, $R_{10}$ and $R_{10}'$ are hydrogen and $R_9$ is

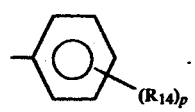

$R_{11}$ is lower alkyl, benzyl, or phenethyl.

$R_{12}$ is hydrogen, lower alkyl, benzyl, or phenethyl.

$R_{13}$ is hydrogen, lower alkyl of 1 to 4 carbons, lower alkoxy of 1 to 4 carbons, lower alkylthio of 1 to 4 carbons, chloro, bromo, fluoro, trifluoromethyl, hydroxy, phenyl, phenoxy, phenylthio, or benzyl.

$R_{14}$ is hydrogen, lower alkyl of 1 to 4 carbons, lower alkoxy of 1 to 4 carbons, lower alkylthio of 1 to 4 carbons, chloro, bromo, fluoro, trifluoromethyl, or hydroxy.

m is zero, one two, three or four.

p is one, two to three provided that p is more than one only if $R_{13}$ or $R_{14}$ is hydrogen, methyl, methoxy, chloro, or fluoro.

$R_{15}$ is hydrogen or lower alkyl of 1 to 4 carbons.

Y is oxygen or sulfur.

$R_{16}$ is lower alkyl of 1 to 4 carbons,

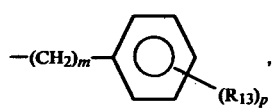

or the $R_{16}$ groups join to complete an unsubstituted 5- or 6-membered ring or said ring in which one or more of the carbons has a lower alkyl of 1 to 4 carbons or a di(lower alkyl of 1 to 4 carbons) substituent.

$R_1$ is hydrogen, lower alkyl, halo substituted lower alkyl, amino substituted lower alkyl, benzyl, or phenethyl.

$R_2$ and $R_4$ are independently selected from hydrogen, lower alkyl, benzyl, benzhydryl, or

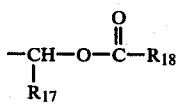

wherein $R_{17}$ is hydrogen, alkyl, cycloalkyl or phenyl, and $R_{18}$ is hydrogen, cycloalkyl, alkyl, phenyl, benzyl, phenethyl, or $R_{17}$ and $R_{18}$ taken together are

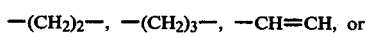 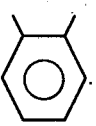

$R_3$ is alkyl, halo substituted lower alkyl, amino substituted lower alkyl, cycloalkyl—$(CH_2)_n$—,

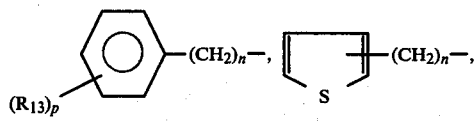

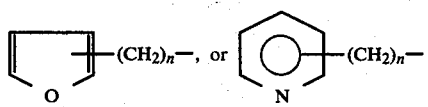

wherein $R_{13}$, m and p are as defined above and n is zero or an integer from 1 to 7.

DETAILED DESCRIPTION OF THE INVENTION

This invention in its broadest aspects relates to the phosphinylmethylaminocarbonyl imino acid compounds of formula I above, to compositions containing such compounds and to the method of using such compounds as anti-hypertensive agents.

The term alkyl used in defining $R_3$ refers to straight or branched chain hydrocarbon radicals having up to ten carbons, for example, methyl, ethyl, propyl, isopropyl, butyl, isobutyl, t-butyl, pentyl, isopentyl, heptyl, octyl, decyl, etc. The term lower alkyl used in defining various symbols refers to straight or branched chain radicals having up to seven carbons. The preferred lower alkyl groups are up to four carbons with methyl and ethyl most preferred. Similarly the terms lower alkoxy and lower alkylthio refer to such lower alkyl groups attached to an oxygen or sulfur.

The term cycloalkyl refers to saturated rings of 3 to 7 carbon atoms with cyclopentyl and cyclohexyl being most preferred.

The term halogen refers to chloro, bromo and fluoro.

The term halo substituted lower alkyl refers to such lower alkyl groups described above in which one or more hydrogens have been replaced by chloro, bromo or fluoro groups such as trifluoromethyl, which is preferred, pentafluoroethyl, 2,2,2-trichloroethyl, chloromethyl, bromomethyl, etc. Similarly, the term amino substituted lower alkyl refers to lower alkyl groups in which one or more hydrogens have been replaced by —$NH_2$, i.e., aminomethyl, 2-aminoethyl, etc.

The symbols

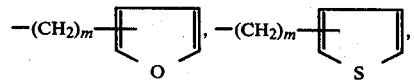

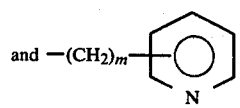

represent that the alkylene bridge is attached to an available carbon atom.

The compounds of formula I wherein $R_1$ is hydrogen may be prepared as follows.

A substituted phosphinyl acetic acid monoester of the formula

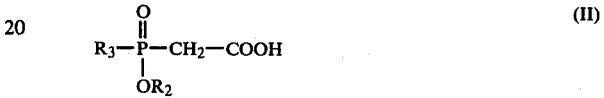

is treated with azidotrimethylsilane in the presence of a coupling agent such as carbonyldiimidazole to yield an acylazide which is rearranged to an isocyanate by refluxing in toluene and then condensed with an imino acid ester of the formula (III)

HX.

In these reactions, the variable $R_2$ is preferably a lower alkyl group such as ethyl, benzyl or benzhydryl and $R_4$ is preferably an ester such as benzyl. Following completion of the reaction the $R_2$ and $R_4$ ester group may be removed to yield the corresponding diacid products, i.e., $R_2$ and $R_4$ are both hydrogen, of formula I.

When $R_3$ is amino substituted lower alkyl in the starting material of formula II the amino group is protected by a phthaloyl group. After completion of the coupling reaction, the protecting group is removed by treatment with hydrazine as the last step of the reaction sequence.

The compounds of formula I wherein $R_1$ is other than hydrogen may be prepared by reacting a diester of the formula

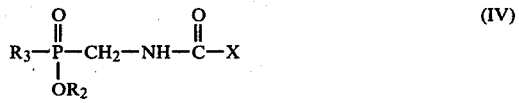

wherein $R_2$ and $R_4$ are ester groups as described above with an alkylating agent of the formula (V)

$R_1$—Br or $R_1$—I in the presence of base such as sodium hydride or potassium t-butoxide wherein $R_1$ is other than hydrogen. Removal of the $R_2$ and $R_4$ ester groups yields the corresponding diacid products.

If $R_1$ is amino substituted lower alkyl then the amino group is protected during this reaction for example by a phthalimido group which is then removed as the last step of the reaction sequence by treatment with hydrazine.

The compounds wherein $R_3$ is other than amino substituted lower alkyl or

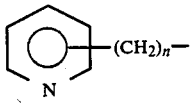

may be prepared by reacting an amine of the formula

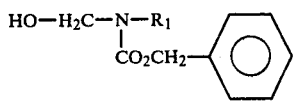 (VI)

with phosphorus pentachloride followed by reaction with a phosphonous diester of the formula

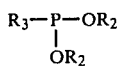 (VII)

to yield

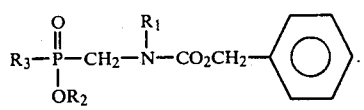 (VIII)

Hydrogenation of the intermediate of formula VIII in the presence of concentrated hydrochloric acid yields the hydrochloric salt of the formula

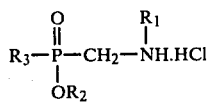 (IX)

which is then coupled with the acid chloride imino acid ester of the formula

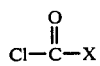 (X)

wherein $R_4$ in the definition of X is preferably benzyl. Removal of the $R_2$ and $R_4$ ester groups following completion of the reaction yields the corresponding diacid products.

The products of formula I wherein either or both of $R_2$ and $R_4$ are lower alkyl, benzyl, or benzhydryl can be hydrogenated, for example, by treating with hydrogen in the presence of a palladium on carbon catalyst or chemically treated such as with sodium hydroxide in aqueous dioxane or with trimethylsilylbromide in dichloromethane to yield the products of formula I wherein $R_2$ and $R_4$ are hydrogen.

The ester products of formula I wherein $R_4$ is

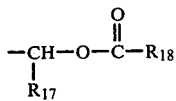

may be obtained by employing the imino acid of formula III or X in the above reactions with the ester group already in place. Such ester reactants can be prepared by treating the imino acid with an acid chloride such as

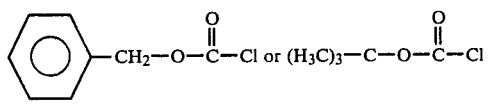

so as to protect the N-atom. The protected acid compound is then reacted in the presence of a base with a compound of the formula

 (XI)

wherein L is a leaving group such as chlorine, bromine, tolysulfonyloxy, etc., followed by removal of the N-protecting group such as by treatment with acid or hydrogenation.

The ester products of formula I wherein $R_4$ is

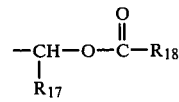

can also be obtained by treating the product of formula I wherein $R_4$ is hydrogen with a molar equivalent of the compound of formula XI. The diester products wherein $R_2$ and $R_4$ are the same and are

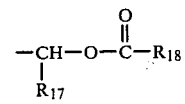

can be obtained by treating the product of formula I wherein $R_2$ and $R_4$ are both hydrogen, an alkali metal or tetraalkyl ammonium salt with two or more equivalents of the compound of formula XI.

The ester products of formula I wherein $R_2$ is

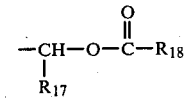

can be obtained by treating the product of formula I wherein $R_2$ is hydrogen, an alkali metal or tetraalkyl ammonium salt and $R_4$ is benzyl or benzhydryl with the compound of formula XI in the presence of base. Removal of the $R_4$ ester group such as by hydrogenation yields the products of formula I wherein $R_2$ is

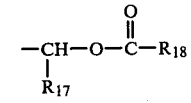

and $R_4$ is hydrogen.

The products of formula I wherein $R_5$ is amino may be obtained by reducing the corresponding products of formula I wherein $R_5$ is azido.

The phosphinyl acetic acid monoesters of formula II wherein $R_3$ is alkyl, halo substituted lower alkyl,

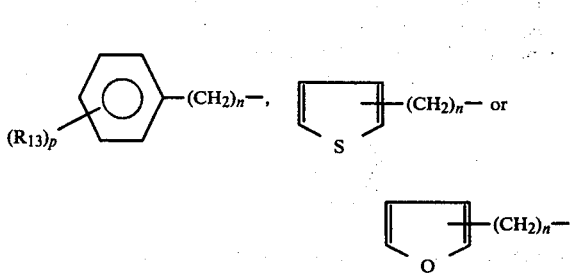

are prepared by reacting a phosphonous diester of the formula

(XII)

with methyl bromoacetate to yield

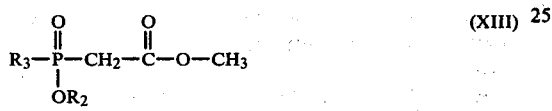

(XIII)

followed by treatment with sodium hydroxide.

The phosphinyl acetic acid monoesters of formula II wherein $R_3$ is

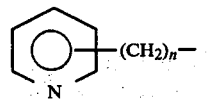

are prepared by reacting a pyridyl alcohol of the formula

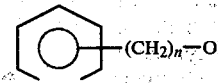

(XIV)

with thionyl chloride to yield the corresponding alkyl-chloride hydrochloride salt of the formula

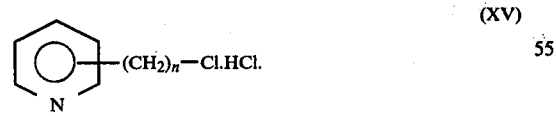

(XV)

The intermediate of formula XV is then reacted with a methylphosphinate of the formula

(XVI)

to yield the intermediate of the formula

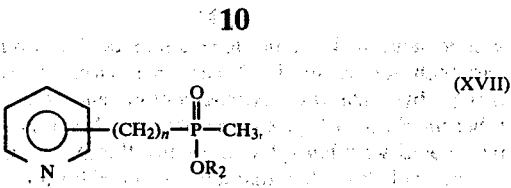

(XVII)

The intermediate of formula XVII is treated with lithium diisopropylamine, carbon dioxide and ethanol/HCl to yield

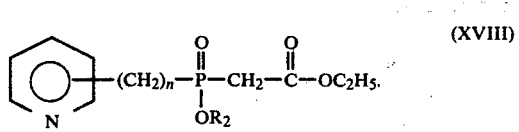

(XVIII)

Treatment with sodium hydroxide yields the monoester starting material of formula II.

The monoester starting material of formula II wherein $R_3$ is protected amino substituted lower alkyl is prepared by reacting a phthalimido protected amino substituted bromo lower alkane of the formula

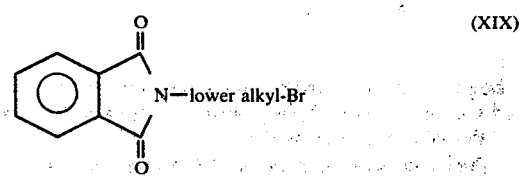

(XIX)

with the phosphonous diester of the formula $$R_2O-P-CH_2-CO_2CH_3 \atop OR_2$$ (XX)

to yield the intermediate of the formula

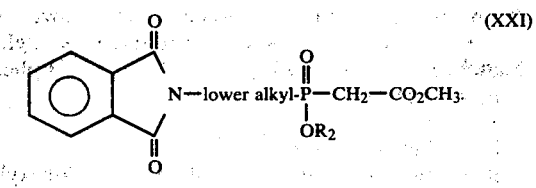

(XXI)

Treatment of intermediate XXI with HCl in aqueous tetrahydrofuran yields the desired monoester of formula II.

The starting materials of formula VI are prepared by reacting a substituted carbamate of the formula

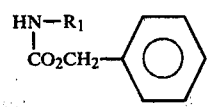

with aqueous formaldehyde and potassium carbonate.

The various imino acids and esters of formula III are described in the literature and U.S. patent applications referred to above. Various substituted prolines are also disclosed by Mauger et al., Chem. Review, Vol. 66, p. 47–86 (1966). When the imino acid is known, it can be readily converted to the ester by conventional means. For example, the esters where $R_4$ is t-butyl can be obtained by treating the corresponding N-carbobenzyloxyimino acid with isobutylene under acidic conditions and then removing the N-carbobenzyloxy protecting group by catalytic hydrogenation and the esters wherein $R_4$ is benzyl can be obtained by treating the imino acid with benzyl alcohol and thionyl chloride.

The acid chloride imino acid esters of formula X are prepared by treating the corresponding imino acid ester of formula III with phosgene in the presence of N-methylmorpholine.

The substituted prolines wherein $R_5$ is the substituted amino group

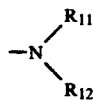

may be prepared by reacting a 4-keto-N-benzyloxycarbonyl proline with the amine

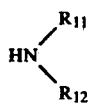

in
the presence of hydrogen and catalyst or in the presence of sodium cyanotrihydridoborate followed by removal of the N-protecting group.

Preferred compounds of this invention with respect to the imino acid or ester part of the structure of formula I are those wherein:

$R_4$ is hydrogen, an alkali metal salt, or $$-\underset{R_{17}}{\underset{|}{CH}}-O-\overset{O}{\underset{\|}{C}}-R_{18},$$

$R_{17}$ is hydrogen, straight or branched chain lower alkyl of 1 to 4 carbons, or cyclohexyl, and $R_{18}$ is a straight or branched chain lower alkyl of 1 to 4 carbons or phenyl.

$R_5$ is hydrogen.
$R_5$ is hydroxy.
$R_5$ is chloro or fluoro.
$R_5$ is lower alkyl of 1 to 4 carbons or cyclohexyl.
$R_5$ is amino.
$R_5$ is —O—lower alkyl wherein lower alkyl is straight or branched chain of 1 to 4 carbons.
$R_5$ is

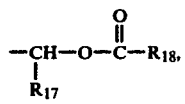

wherein m is zero, one or two, $R_{13}$ is hydrogen, methyl, methoxy, methylthio, chloro, bromo, fluoro, or hydroxy.
$R_5$ is

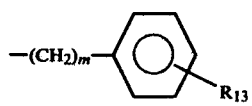

1-naphthyloxy or 2-naphthyloxy wherein m is zero, one or two, and $R_{13}$ is hydrogen, methyl, methoxy, methylthio, chloro, bromo, fluoro, or hydroxy.

$R_5$ is —S—lower alkyl wherein lower alkyl is straight or branched chain of 1 to 4 carbons.

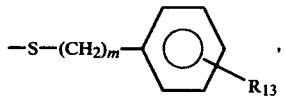

1-naphthylthio, or 2-naphthylthio wherein m is zero, one or two, and $R_{13}$ is hydrogen, methyl, methoxy, methylthio, chloro, bromo, fluoro, or hydroxy.

$R_6$ is —O—lower alkyl wherein lower alkyl is straight or branched chain of 1 to 4 carbons.

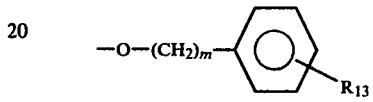

$R_6$ is
wherein m is zero, one or two, and $R_{13}$ is hydrogen, methyl, methoxy, methylthio, chloro, bromo, fluoro, or hydroxy.

$R_6$ is —S—lower alkyl wherein lower alkyl is straight or branched chain of 1 to 4 carbons.

$R_6$ is

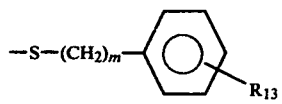

wherein m is zero, one or two, and $R_{13}$ is hydrogen, methyl, methoxy, methylthio, chloro, bromo, fluoro, or hydroxy.

$R_7$ is phenyl, 2-hydroxyphenyl, or 4-hydroxyphenyl.
$R_8$ are both fluoro or chloro.
$R_8$ are both —Y—$R_{16}$ wherein Y is O or S, $R_{16}$ is straight or branched chain alkyl of 1 to 4 carbons or the $R_{16}$ groups join to complete an unsubstituted 5- or 6-membered ring or said ring in which one or more of the carbons has a methyl or dimethyl substituent.

$R_9$, $R_9'$, $R_{10}$ and $R_{10}'$ are all hydrogen, or $R_9$ is phenyl, 2-hydroxyphenyl or 4-hydroxyphenyl and $R_9'$, $R_{10}$ and $R_{10}'$ are hydrogen Most preferred compounds of this invention with respect to the imino acid or ester part of the structure of formula I are those wherein:
X is

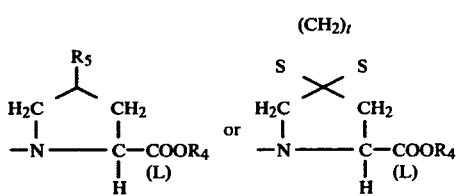

$R_4$ is hydrogen,

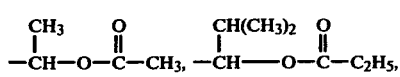

-continued

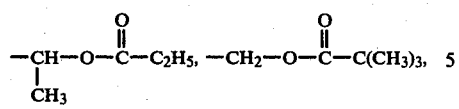

or an alkali metal salt.

$R_5$ is hydrogen.

$R_5$ is cyclohexyl.

$R_5$ is lower alkoxy of 1 to 4 carbons.

$R_5$ is

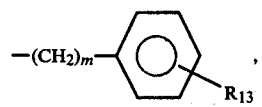

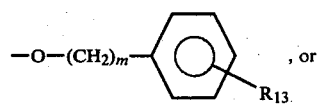, or

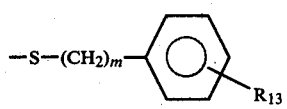

wherein m is zero, one, or two and $R_{13}$ is hydrogen, methyl, methoxy, methylthio, Cl, Br, F or hydroxy.

t is two or three, especially where t is two.

Preferred compounds of this invention with respect to the phosphinylmethylaminocarbonyl sidechain are those wherein:

$R_2$ is hydrogen, an alkali metal salt, lower alkyl of 1 to 4 carbons, benzyl, or

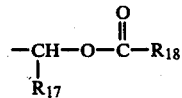

wherein $R_{17}$ is hydrogen, straight or branched chain lower alkyl of 1 to 4 carbons, or cyclohexyl, and $R_{18}$ is straight or branched chain lower alkyl of 1 to 4 carbons or phenyl, especially hydrogen, alkali metal salt, ethyl,

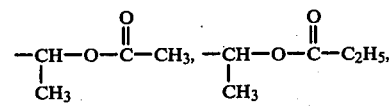

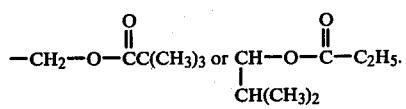

$R_1$ is hydrogen, lower alkyl of 1 to 4 carbons, or amino substituted lower alkyl of 1 to 4 carbons especially hydrogen or ethyl.

$R_3$ is alkyl of 1 to 10 carbons,

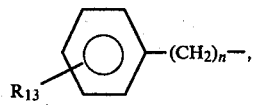

—$(CH_2)_n$-cycloalkyl wherein cycloalkyl is of 5 or 6 carbons, amino substituted lower alkyl,

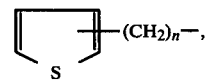

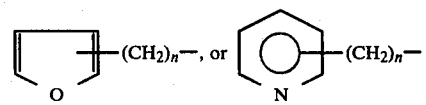

wherein n is zero or an integer from 1 to 4, $R_{13}$ is hydrogen, methyl, methoxy, methylthio, chloro, bromo, fluoro, or hydroxy, especially

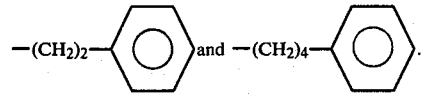

The compounds of this invention wherein at least one of $R_2$ or $R_4$ is hydrogen, form basic salts with various inorganic and organic bases which are also within the scope of the invention. Such salts include ammonium salts, alkali metal salts like lithium, sodium and potassium salts (which are preferred), alkaline earth metal salts like calcium and magnesium salts, salts with organic bases, e.g., dicyclohexylamine salt, benzathine, N-methyl-D-glucamine, hydrabamine salts, salts with amino acids like arginine, lysine and the like. The nontoxic, physiologically acceptable salts are preferred, although other salts are also useful, e.g., in isolating or purifying the product. The salts are formed using conventional techniques.

As shown above, the imino acid or ester portion of the molecule of the products of formula I represented by X is in the L-configuration. The products of formula I wherein the imino acid ring is monosubstituted give rise to cis-trans isomerism. The configuration of the final product will depend upon the configuration of the $R_5$, $R_6$ and $R_7$ substituent in the starting material of formula III or X.

The compounds of formula I, and the physiologically acceptable salts thereof, are hypotensive agents. They inhibit the conversion of the decapeptide angiotensin I to angiotensin II and, therefore, are useful in reducing or relieving angiotensin related hypertension. The action of the enzyme renin or angiotensinogen, a pseudoglobulin in blood plasma, produces angiotensin I. Angiotensin I is converted by angiotensin converting enzyme (ACE) to angiotensin II. The latter is an active pressor substance which has been implicated as the causative agent in several forms of hypertension in various mammalian species, e.g., humans. The compounds of this invention intervene in the angiotensinogen→(renin)→angiotensin I→angiotensin II sequence by inhibiting angiotensin converting enzyme and reducing or eliminating the formation of the pressor substance angiotensin II. Thus by the administration of a composition containing one (or a combination) of the compounds of this invention, angiotensin dependent hypertension in a species of mammal (e.g., humans) suffering therefrom is alleviated. A single dose, or preferably two to four divided daily doses, provided on a basis of about 0.1 to 100 mg. per kilogram of body weight per day is appropriate to reduce blood pressure. The substance is preferably administered orally, but parenteral routes such as the subcutaneous, intramuscular, intravenous or intraperitoneal routes can also be employed.

The compounds of this invention can also be formulated in combination with a diuretic for the treatment of hypertension. A combination product comprising a compound of this invention and a diuretic can be administered in an effective amount which comprises a total daily dosage of about 30 to 600 mg., preferably about 30 to 330 mg. of a compound of this invention, and about 15 to 300 mg., preferably about 15 to 200 mg. of the diuretic, to a mammalian species in need thereof. Exemplary of the diuretics contemplated for use in combination with a compound of this invention are the thiazide diuretics, e.g., chlorothiazide, hydrochlorothiazide, flumethiazide, hydroflumethiazide, bendroflumethiaside, methyclothiazide, trichloromethiazide, polythiazide or benzthiazide as well as ethacrynic acid, ticrynafen, chlorthalidone, furosemide, musolimine, bumetanide, triamterene, amiloride and spironolactone and salts of such compounds.

The compounds of formula I can be formulated for use in the reduction of blood pressure in compositions such as tablets, capsules or elixirs for oral administration, or in sterile solutions or suspensions for parenteral administration. About 10 to 500 mg. of a compound of formula I is compounded with physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

The following examples are illustrative of the invention. Temperatures are given in degrees centigrade. AG-50W-X8 refers to a crosslinked polystyrene divinylbenzene sulfonic acid cation exchange resin. HP-20 refers to a porous crosslinked polystyrene-divinyl benzene polymer resin.

EXAMPLE 1

1-[[[[Hydroxy(4-phenylbutyl)phosphinyl]methyl]amino]carbonyl]-L-proline, dilithium salt (a) (4-Phenylbutyl)phosphonous acid, diethyl ester Magnesium metal (4.8 g., 0.2 mole) was slurried in 50 ml. of diethyl ether and a solution of 1-chloro-4-phenylbutane (36.4 g., 0.22 mole) in 100 ml. of diethyl ether was added dropwise at a rate to maintain gentle reflux, followed by stirring at reflux for one hour. After cooling, and filtration under argon, the Grignard solution (0.147 mole by titration) was added dropwise to a chilled (0°) solution of diethylchlorophosphite (25.7 g., 0.16 mole) in 100 ml. of ether, at a rate to maintain the internal temperature at 0°-10°. Following the addition, the mixture was heated at reflux for 1.5 hours. After filtration and concentration at atmospheric pressure, under argon, the residue was fractionated at reduced pressure to give 29.7 g. of (4-phenylbutyl)phosphonous acid, diethyl ester; b.p. 110°-113° at 0.09-0.1 mm.

(b) [Ethoxy(4-phenylbutyl)phosphinyl]acetic acid, methyl ester

A mixture of 16.9 g. (0.11 mole) of methyl bromoacetate and 5.0 g. (0.019 mole) of (4-phenylbutyl)phosphonous acid, diethyl ester was heated on a 140°-150° oil bath until distillation of ethyl bromide was detected. An additional 16 g. (0.063 mole) of (4-phenylbutyl)phosphonous acid, diethyl ester was then gradually added to the reaction mixture. Heating was then continued for 45 minutes. After cooling to 100°, excess reagent was removed in vacuo to give 25 g. of crude product ($R_f$=0.25 silica gel/ethyl acetate). Impurities with higher $R_f$ values were separated by flash chromatography using ethyl acetate. As a result, 18.3 g. of [ethoxy(4-phenylbutyl)phosphinyl]acetic acid, methyl ester were obtained.

(c) [Ethoxy(4-phenylbutyl)phosphinyl]acetic acid

A solution of 15 g. (0.05 mole) of [ethoxy(4-phenylbutyl)phosphinyl]acetic acid, methyl ester in 51 ml. of 0.99 N sodium hydroxide (0.05 mole) was stirred for 30 minutes at room temperature. After extraction with ether, the solution was treated with 8.5 ml. of 5 N hydrochloric acid. The product was extracted into ethyl acetate, dried and the solvent evaporated in vacuo to give 13.6 g. of [ethoxy(4-phenylbutyl)phosphinyl]acetic acid as an oil product. $R_f$=0.75 on silica gel using dichloromethane/acetic acid/methanol (8:1:1).

Anal. calc'd. for $C_{14}H_{21}O_4P$: C, 59.14; H, 7.44. Found: C, 57.85; H, 7.46.

(d) 1-[[[[Ethoxy(4-phenylbutyl)phosphinyl]methyl]amino]carbonyl]-L-proline, phenylmethyl ester A solution of [ethoxy(4-phenylbutyl)phosphinyl]acetic acid (1.94 g., 6.83 mmole) in 15 ml. of dry toluene was treated with carbonyldiimidazole (1.15 g., 7.10 mmole) and stirred at 0° (ice bath) for one hour. The resulting solution was treated with azidotrimethylsilane (1.5 ml., 11.3 mmole) and allowed to warm to room temperature. After 30 minutes, the mixture was diluted with toluene (approximately 30 ml.) and washed successively with 5% potassium bisulfate solution (twice) and saturated sodium chloride solution, dried over $Na_2SO_4$ and evaporated to give 2.1 g. of crude acylazide. Tlc (acetone-dichloromethane; 1:2) major spot at $R_f$=0.57, IR (film)2150 cm$^{-1}$ ($N_3$).

The crude acylazide (2.1 g.) was taken up in 15 ml. of dry toluene and heated at 90° (bath temperature) until the nitrogen evolution had stopped (about 30 minutes). IR (film) 2250 cm$^{-1}$ (—NCO). The cooled mixture was treated with L-proline, phenylmethyl ester hydrochloride (1.75 g., 7.25 mmole) and triethylamine (1.0 ml., 7.23 mmole) and stirred overnight at room temperature. The mixture was partitioned between ethyl acetate —5% potassium bisulfate. The ethyl acetate layer was washed successively with 5% potassium bisulfate, saturated sodium bicarbonate and saturated sodium chloride, dried over $Na_2SO_4$ and evaporated. The residue (3.0 g.) was purified by flash chromatography on silica gel (115 g.) eluting first with dichloromethane-acetone (3:2) then acetone to give 2.44 g. of 1-[[[[ethoxy(4-phenylbutyl)phosphinyl]methyl]amino]carbonyl]-L-proline, phenylmethyl ester as a colorless viscous oil. $R_f$(acetone-dichloromethane, 1:2)=0.21.

(e) 1-[[[[Hydroxy(4-phenylbutyl)phosphinyl]methyl]amino]carbonyl]-L-proline, phenylmethyl ester A solution of 1-[[[[ethoxy(4-phenylbutyl)phosphinyl]methyl]amino]carbonyl]-L-proline, phenylmethyl ester (2.3 g., 4.73 mmole) in dry dichloromethane (10 ml.) under argon was treated via syringe with trimethylsilylbromide (1.0 ml., 7.58 mmole) and stirred overnight at room temperature. The excess trimethylsilylbromide and dichloromethane were removed in vacuo and the residue was partitioned between ethyl acetate-water. The ethyl acetate layer was washed with saturated sodium chloride solution, dried over $MgSO_4$ and evaporated. The residue (2.15 g.) was purified by flash chromatography on silica gel (100 g.) eluting with acetic acid-methanol-dichloromethane (1:1:20) to give 2.1 g. of pure 1-[[[[hydroxy(4-phenylbutyl)phosphinyl]-methyl]amino]carbonyl]-L-proline, phenylmethyl ester as a colorless glass. $R_f$ (acetic acid-methanol-dichloromethane, 1:1:20) = 0.37.

(f) 1-[[[[Hydroxy(4-phenylbutyl)phosphinyl]methyl]amino]carbonyl]-L-proline

A solution of 1-[[[[hydroxy(4-phenylbutyl)phosphinyl]methyl]amino]carbonyl]-L-proline, phenylmethyl ester (2.1 g., 4.58 mmole) in 50 ml. of methanol was treated with 10% palladium on carbon catalyst (400 mg.) and hydrogenated in a Parr apparatus at an initial pressure of 50 psi for 4.5 hours. The catalyst was filtered off through celite and the filtrate evaporated to dryness. The residue (1.7 g.) was taken up in 10 ml. of tetrahydrofuran and added dropwise to 125 ml. of ethyl acetate with vigorous stirring. The white precipitate was collected, washed thoroughly with ethyl acetate and air dried to give 1.36 g. of 1-[[[[hydroxy(4-phenylbutyl)phosphinyl]methyl]amino]carbonyl]-L-proline as an off-white solid; m.p. 118°–125° (dec.). $R_f$ (dichloromethane-methanol-acetic acid; 8:1:1) = 0.32. IR (KBr): 1710 $cm^{-1}$ ($CO_2H$); 1610, 1535 $cm^{-1}$ (—NH.CON<).

(g) 1-[[[[Hydroxy(4-phenylbutyl)phosphinyl]methyl]amino]carbonyl]-L-proline, dilithium salt A solution of the diacid product from part (f) (1.1 g., 2.99 mmole) in 1 N lithium hydroxide (4.0 ml., 4.0 mmole) was passed through a column of AG-50W-X8 ($Li^+$, 50 ml. settled volume). The eluate was filtered (millipore) and lyophilized to give 980 mg. of 1-[[[[hydroxy(4-phenylbutyl)phosphinyl]methyl]amino]carbonyl]-L-proline, dilithium salt as a colorless lyophilizate.

Anal. calc'd. for: $C_{17}H_{23}N_2O_5PLi_2 \cdot H_2O$: C, 51.27; H, 6.33; N, 7.03; P, 7.8. Found: C, 51.35; H, 6.37; N, 6.84; P, 7.7.

EXAMPLES 2–47

Following the procedure of Example 1 but employing the substituted acetic acid shown in Col. I and the imino acid shown in Col. II one obtains the compound shown in Col. III. Removal of the $R_2$ and $R_4$ ester groups yields the corresponding diacid products ($R_2$ and $R_4$ are both hydrogen).

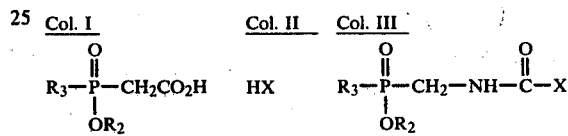

| Example | $R_3$ | $R_2$ | X |
|---|---|---|---|
| 2 | 6-) | $-C_2H_5$ | |
| 3 | Cl-ph-(CH2)3- | $-C_2H_5$ | |
| 4 | H3CO-ph-(CH2)2- | $-C_2H_5$ | |
| 5 | ph- | $-C_2H_5$ | |

-continued

| Example | R₃ | R₂ | X |
|---|---|---|---|
| 6 | 3,5-dichlorobenzyl (CH₂ attached to 2,4-Cl₂-phenyl) | —C₂H₅ | piperidine with S—CH₂—C₆H₄—F substituent, N—H, COOCH₂C₆H₅ (L) |
| 7 | H₃C—(CH₂)₅— | —C₂H₅ | piperidine with CH₂—C₆H₅ substituent, N—H, COOCH₂C₆H₅ (L) |
| 8 | cyclohexyl- | —C₂H₅ | piperidine with N₃ substituent, N—H, COOCH₂C₆H₅ (L) |
| 9 | H₅C₂— | —CH₂—C₆H₅ | piperidine, N, COOCH₂C₆H₅ (L) |
| 10 | H₃C—C₆H₄—(CH₂)₂— | —C₂H₅ | azetidine, N—H, COOCH₂C₆H₅ (L) |
| 11 | F₃C—CH₂— | —C₂H₅ | piperidine with =O substituent, N—H, COOCH₂C₆H₅ (L) |
| 12 | Cl₃CH₂C— | —C₂H₅ | piperidine with Cl substituent, N—H, COOCH₂C₆H₅ (L) |
| 13 | thiophene-2-yl-(CH₂)₂— | —CH(C₆H₅)₂ | piperidine with OCH₃ substituent, N—H, COOCH₂C₆H₅ (L) |
| 14 | thiophene-3-yl-CH₂— | —C₂H₅ | piperidine with N(CH₃)₂ substituent, N—H, COOCH₂C₆H₅ (L) |

-continued

| Example | R₃ | R₂ | X |
|---|---|---|---|
| 15 | (2-furyl) | —C₂H₅ | pipecolate-type: 4-(NHCOCH₃) substituted piperidine, —N(H)—CH—COOCH₂C₆H₅ (L) |
| 16 | (2-furyl)-(CH₂)₃— | —C₂H₅ | 4-(NHCOCH₂C₆H₅) substituted piperidine, —N(H)—CH—COOCH₂C₆H₅ (L) |
| 17 | 4-pyridyl-CH₂— | —C₂H₅ | 4-phenyl substituted piperidine, —N(H)—CH—COOCH₂C₆H₅ (L) |
| 18 | 2-pyridyl-CH₂— | —C₂H₅ | 4-((CH₂)₂C₆H₅) substituted piperidine, —N(H)—CH—COOCH₂C₆H₅ (L) |
| 19 | 3-pyridyl-(CH₂)₄— | —C₂H₅ | 4-(CH₂-2-thienyl) substituted piperidine, —N(H)—CH—COOCH₂C₆H₅ (L) |
| 20 | C₆H₅—(CH₂)₂— | —CH₂C₆H₅ | 4-(CH₂-2-naphthyl) substituted piperidine, —N(H)—CH—COOCH₂C₆H₅ (L) |
| 21 | C₆H₅—(CH₂)— | —C₂H₅ | 4-(CH₂-4-biphenyl) substituted piperidine, —N(H)—CH—COOCH₂C₆H₅ (L) |

-continued
| Example | R₃ | R₂ | X |
|---|---|---|---|
| 22 | 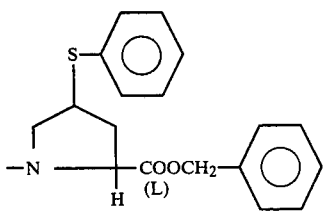 | —C₂H₅ | 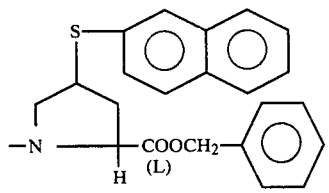 |
| 23 | H₃C—(H₂C)₃— | —C₂H₅ | 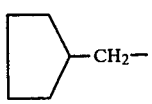 |
| 24 | 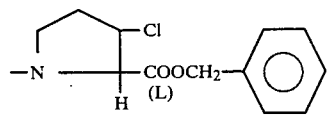 | —C₂H₅ | 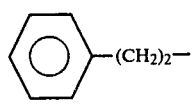 |
| 25 | 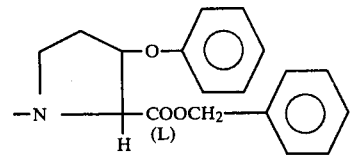 | —C₂H₅ | 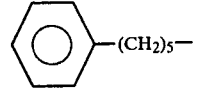 |
| 26 | 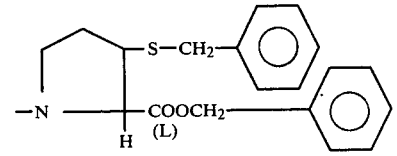 | —C₂H₅ | 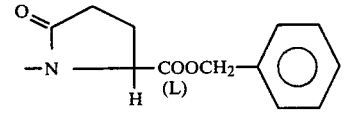 |
| 27 | H₃C—(H₂C)₃— | —C₂H₅ | 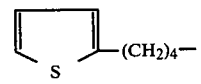 |
| 28 | 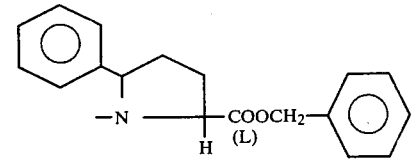 | —C₂H₅ | 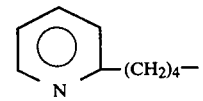 |
| 29 | 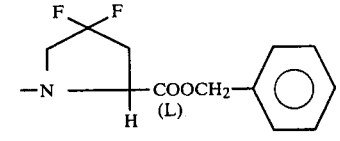 | —C₂H₅ | 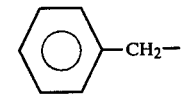 |
| 30 | 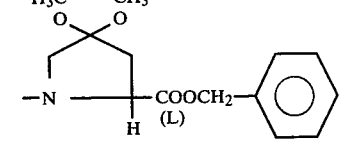 | —C₂H₅ | |

-continued

| Example | R₃ | R₂ | X |
|---|---|---|---|
| 31 | C₆H₅—(CH₂)₃— | —C₂H₅ | 2-methyl-1,3-dioxane-5-yl linked via pyrrolidine-type ring with —N(H)—CH(COOCH₂C₆H₅)— (L) |
| 32 | 2-furyl-CH₂— | —C₂H₅ | 1,3-dithiane spiro ring with —N(H)—CH(COOCH₂C₆H₅)— (L) |
| 33 | F₃C— | —C₂H₅ | 1,3-dithiane spiro ring with —N(H)—CH(COOCH₂C₆H₅)— (L) |
| 34 | C₆H₅—(CH₂)₄— | —C₂H₅ | 2,2-dimethyl-1,3-dithiane spiro ring with —N(H)—CH(COOCH₂C₆H₅)— (L) |
| 35 | 4-CH₃—C₆H₄—(CH₂)₂— | —C₂H₅ | 2,5-dihydro-1H-pyrrole ring —N—CH(COOCH₂C₆H₅)— (L) |
| 36 | C₆H₅—CH₂— | —C₂H₅ | thiazolidine ring —N—CH(COOCH₂C₆H₅)(H)— (L) |
| 37 | C₆H₅—(CH₂)₄— | —C₂H₅ | 5,5-dimethylthiazolidine ring —N—CH(COOCH₂C₆H₅)(H)— (L) |
| 38 | C₆H₅—(CH₂)₂— | —C₂H₅ | 2-phenylthiazolidine ring —N—CH(COOCH₂C₆H₅)(H)— (L) |

| Example | R₃ | R₂ | X |
|---|---|---|---|
| 39 | phenyl | —C₂H₅ | (2-substituted benzyl)-N-CH(COOCH₂Ph)- (L) |
| 40 | phenyl-(CH₂)₄— | —C₂H₅ | (2-substituted benzyl)-N-CH(COOCH₂Ph)- (L) |
| 41 | phenyl-(CH₂)₂— | —C₂H₅ | tetrahydroisoquinoline-N-CH(COOCH₂Ph)- (L) |
| 42 | phthalimido-(CH₂)₆— | —C₂H₅ | —N-CH(COOCH₂Ph)- (L) |
| 43 | phthalimido-(CH₂)₂— | —C₂H₅ | β-phenyl substituted -N-CH(COOCH₂Ph)- (L) |
| 44 | phenyl-(CH₂)₂— | —CH₂Ph | —N-CH(C(O)-O-CH₂-C(O)-C(CH₃)₃)- (L) |
| 45 | phenyl-(CH₂)₄— | —CH₂Ph | phenylthio substituted -N-CH(C(O)-O-CH(C₂H₅)-C(O)-CH₃)- (L) |
| 46 | H₃C—(H₂C)₅— | —CH₂Ph | —N-CH(C(O)-O-CH₂-C(O)-Ph)- (L) |

| Example | R₃ | R₂ | X |
|---|---|---|---|
| 47 | phenyl-(CH₂)₂— | —CH₂-phenyl | —N(H)—CH₂CH₂—P(=O)(O—)—O—C(=O)-phenyl (L) |

-continued

Reduction of the product of Example 8 yields the corresponding 4-amino product. Similarly, the 4-keto product of Example 11 can be reacted to yield various 4-substituted amino products. The protecting groups shown in Examples 42 and 43 are removed following completion of the coupling reaction. The R₄ ester groups shown in Examples 44 to 47 would not be removed.

EXAMPLE 48

1-[[Ethyl[[hydroxy(4-phenylbutyl)phosphinyl]methyl]-amino]carbonyl]-L-proline, dilithium salt (a) Ethylcarbamic acid, phenylmethyl ester Gaseous ethylamine was bubbled through a solution of benzyl chloroformate (9.0 ml., 60 mmole) in 200 ml. of dry tetrahydrofuran for one hour. The heterogeneous mixture was treated with triethylamine (10 ml., 72 mmole) and stirred at room temperature for 20 minutes. The reaction mixture was diluted with ethyl acetate and washed with 5% potassium bisulfate, water, brine, dried (MgSO₄), and evaporated. The residue (10.2 g.) crystallized upon standing at 0°. The white solid was triturated with cold hexane and then collected by filtration to give 9.3 g. of ethylcarbamic acid, phenylmethyl ester as a white solid; m.p. approximately at room temperature. Tlc (ethyl acetate) single spot at $R_f=0.9$.

(b) Ethyl(hydroxymethyl)carbamic acid, phenylmethyl ester

A mixture of ethylcarbamic acid, phenylmethyl ester (8.5 g., 47.4 mmole), aqueous formaldehyde (38.0 ml., 0.47 mole), potassium carbonate (6.6 g.), and dioxane (40 ml.) was refluxed under argon for 3.5 hours. The cooled reaction mixture was diluted with ethyl acetate and washed with water, saturated sodium bicarbonate, brine, dried (MgSO₄), and evaporated. The residue (13.5 g.) was chromatographed on silica (300 g.) eluting with hexane/ethyl acetate (5:2) to give 7.6 g. (36.3 mmole) of ethyl (hydroxymethyl) carbamic acid, phenylmethyl ester as a liquid. Tlc (hexane/ethyl acetate, 2:1) single spot at $R_f=0.3$.

(c) [[Ethoxy(4-phenylbutyl)phosphinyl]methyl]-ethylcarbamic acid, phenylmethyl ester A mixture of ethyl (hydroxymethyl)carbamic acid, phenylmethyl ester (4.0 g., 19.1 mmole), and dry dichloromethane (10 ml.) under argon at room temperature was treated with phosphorus pentachloride (4.2 g., 21 mmole). An exotherm was observed. After one hour the dichloromethane and phosphorus oxychloride were removed in vacuo. The residue was diluted with toluene then evaporated to remove any residual phosphorus oxychloride. The residue was taken up in dry toluene (10 ml.) and treated with diethyl (4-phenylbutyl)phosphonite (5.8 g., 1.2 eq.) at 25° in an argon atmosphere. The reaction mixture was refluxed for one hour and then evaporated to dryness. The residue (approximately 11 g.) was chromatographed on silica (30 g.) eluting with hexane/acetone (5:2) to obtain 5.2 g. (12.4 mmole) of [[ethoxy(4-phenylbutyl)phosphinyl]methyl]ethylcarbamic acid, phenylmethyl ester as an oil. Tlc (hexane-/acetone, 5:2) single spot at $R_f=0.3$.

(d) [(Ethylamino)methyl](4-phenylbutyl)phosphinic acid, ethyl ester, hydrochloride A mixture of [[ethoxy(4-phenylbutyl)phosphinyl]-methyl]ethylcarbamic acid, phenylmethyl ester (4.6 g., 11 mmole), 10% palladium on carbon catalyst (1.5 g.), methanol (60 ml.), and 1 N hydrochloric acid (20 ml., 20 mmole) was shaken on the Parr apparatus at 49 psi hydrogen for 16 hours. The catalyst was removed by filtration through Celite and the methanol, water, and excess hydrochloric acid were stripped. Azeotropic removal of water and hydrochloric acid was effected using toluene to give 3.2 g. (10.0 mmole) of [(ethylamino)methyl](4-phenylbutyl)phosphinic acid, ethyl ester, hydrochloride as an oil which solidified on prolonged standing. Tlc (isopropanol/conc. NH₄OH/-water; 7:2:1) single spot at $R_f=0.95$.

(e) 1-[[Ethyl[[ethoxy(4-phenylbutyl)phosphinyl]methyl]amino]carbonyl]-L-proline, phenylmethyl ester A 12.5% phosgene/benzene (12.0 ml., approximately 15 mmole) solution and dry dichloromethane (20 ml.) in an argon atmosphere at −20° (carbon tetrachloride/dry ice bath) was treated dropwise over 10 minutes with a mixture of N-methylmorpholine (1.8 ml., 16.6 mmole), L-proline, phenylmethyl ester, hydrochloride (2.0 g., 8.3 mmole), and dichloromethane (10 ml.). After stirring at −20° for 30 minutes the bath was removed and the reaction mixture was stirred for an additional 15 minutes. The benzene, dichloromethane and excess phosgene were removed in vacuo to leave a white solid. The residue was taken up in dry dichloromethane (15 ml.) and treated with N-methylmorpholine (2.6 ml., 25 mmole) and [(ethylamino)methyl](4-phenylbutyl)phosphinic acid, ethyl ester, hydrochloride (2.6 g., 8.3 mmole) at room temperature under argon. After 16 hours, the reaction mixture was diluted with ethyl acetate, washed with saturated sodium bicarbonate, 5% potassium bisulfate, brine, dried (MgSO₄), and evaporated. The residue (2.2 g.) was chromatographed on silica (100 g.) eluting with hexane/acetone (12:1) followed by hexane/acetone (1:1). Evaporation yielded 800 mg. (1.56 mmole) of 1-[[ethyl[[ethoxy(4-phenyl-butyl)phosphinyl]methyl]amino]carbonyl]-L-proline, phenylmethyl ester as an oil. Tlc (hexane/acetone, 1:1) single spot at $R_f=0.4$.

(f) 1-[[Ethyl[[ethoxy(4-phenylbutyl)phosphinyl]-methyl]amino]carbonyl]-L-proline A mixture of 1-[[ethyl[[ethoxy(4-phenylbutyl)-phosphinyl]methyl]carbonyl]-L-proline, phenylmethyl ester (800 mg., 1.56 mmole), methanol (50 ml.), and 10% palladium on carbon catalyst (150 mg.) was hydrogenated on the Parr apparatus at 50 psi for 1.5 hours. The catalyst was removed by filtration (Celite bed) and the methanol stripped to give 600 mg. residue. This residue was passed through a pad of silica eluting with dichloromethane/methanol/acetic acid (100/5/5) to remove a polar impurity. After evaporation and azeotropic removal (toluene) of residual acetic acid, 550 mg. of 1-[[ethyl[[ethoxy(4-phenylbutyl)phosphinyl]methyl]amino]carbonyl]-L-proline was obtained as an oil. Tlc (dichloromethane/methanol/acetic acid; 100:5:5) single spot at $R_f=0.6$.

(g) 1-[[Ethyl[[hydroxy(4-phenylbutyl)phosphinyl]methyl]amino]carbonyl]-L-proline, dilithium salt A mixture of 550 mg. (1.18 mmole) of 1-[[ethyl[[ethoxy(4-phenylbutyl)phosphinyl]methyl]amino]carbonyl]-L-proline in dry dichloromethane (4 ml.) was treated with trimethylsilylbromide (0.36 ml., 2.0 eq.) via gas tight syringe in an argon atmosphere at room temperature. After 2.5 hours, the dichloromethane and excess trimethylsilylbromide were removed in vacuo. The residue was taken up in ethyl acetate and water. The layers were separated and the ethyl acetate portion was washed with water (twice), brine, dried ($MgSO_4$), and evaporated. The residue (450 mg.) was passed through an AG-50W-X2 ($Li^+$) 30 ml. column eluting with water. The desired fractions were combined and lyophilized. The white lyophilizate (400 mg.) was chromatographed on an HP-20 (200 ml.) column eluting with water→acetonitrile (0→90%). The water and acetonitrile were stripped and the residue taken up in water, filtered (millipore), and lyophilized to give 340 mg. (0.83 mmole) of 1-[[ethyl[[hydroxy(4-phenylbutyl)phosphinyl]methyl]amino]carbonyl]-L-proline, dilithium salt as a white solid. Tlc (isopropanol/conc. $NH_4OH$/water, 7:2:1) single spot at $R_f=0.7$.

Anal. calc'd. for $C_{19}H_{27}N_2O_5P.1.25H_2O$: C, 52.97; H, 6.90; N, 6.50; P, 7.2. Found: C, 52.97; H, 6.74; N, 6.60; P, 7.1.

EXAMPLE 49

1-[[Ethyl[[hydroxy(2-phenylethyl)phosphinyl]methyl]amino]carbonyl]-L-proline, dilithium salt (a) [[Ethoxy(2-phenylethyl)phosphinyl]methyl]ethylcarbamic acid, phenylmethyl ester A mixture of ethyl(hydroxymethyl) carbamic acid, phenylmethyl ester (5.2 g., 25 mmole) in dry dichloromethane (20 ml.) under argon at room temperature was treated with phosphorus pentachloride (5.7 g., 27.5 mmole). An exotherm was observed. After one hour the dichloromethane and phosphorus oxychloride were removed in vacuo. The residue was diluted with toluene then evaporated to remove any residual phosphorus oxychloride. The residue was taken up in dry toluene (20 ml.) and treated with diethyl (2-phenylethyl) phosphonite (6.2 g., 1.1 eq.) at 25° in an argon atmosphere. The reaction mixture was refluxed for 3 hours then evaporated to dryness. The residue (10.2 g.) was chromatographed on silica (350 g.) eluting with ethyl acetate to give 6.9 g. (17.7 mmole) of [[ethoxy(2-phenylethyl)phosphinyl]methyl]ethylcarbamic acid, phenylmethyl ester. Tlc (ethylacetate) single spot at $R_f=0.3$.

(b) [(Ethylamino)methyl](2-phenylethyl)phosphinic acid, ethyl ester, hydrochloride A mixture of [[ethoxy(2-phenylethyl)phosphinyl]methyl]ethylcarbamic acid, phenylmethyl ester (6.6 g., 16.9 mmole), methanol (75 ml.), 1 N hydrochloric acid (20 ml., 20 mmole), and 10% palladium on carbon catalyst (2.0 g.) was hydrogenated in a Parr apparatus at 50 psi for 16 hours. The catalyst was removed by filtration (Celite bed) and the solvent stripped. The residue was triturated with ether and the resulting solid was collected by filtration, washed with ether (three times), and dried in vacuo to give 4.1 g. (14 mmole) of [(ethylamino)-methyl](2-phenylethyl)phosphinic acid, ethyl ester, hydrochloride as a white solid; m.p. 139°–141.5°.

Anal. calc'd. for $C_{13}H_{23}NO_2PCl.0.3H_2O$: C, 52.54; H, 8.01; N, 4.71; P, 10.4; Cl, 11.93. Found: C, 52.54; H, 7.86; N, 4.61; P, 10.5; Cl, 12.35.

(c) 1-[[Ethyl[[ethoxy(2-phenylethyl)phosphinyl]methyl]amino]carbonyl]-L-proline, phenylmethyl ester A mixture of 12.5% phosgene/benzene (20 ml., 25 mmole) and dry dichloromethane (25 ml.) in an argon atmosphere at −20° (dry ice/carbon tetrachloride) was treated dropwise over 10 minutes with a mixture of N-methylmorpholine (4.4 ml., 39 mmole), L-proline, phenylmethyl ester, hydrochloride (4.7 g., 20 mmole) and dichloromethane (10 ml.). The ice bath was removed and the mixture was stirred for 30 minutes. The dichloromethane, benzene, and excess phosgene were removed in vacuo. The residue was taken up in dichloromethane and treated with [(ethylamino) methyl](2-phenylethyl)phosphinic acid, ethyl ester, hydrochloride (3.8 g., 13 mmole) and N-methylmorpholine (4.4 ml., 39 mmole in an argon atmosphere at 25°. After stirring at room temperature for 16 hours and at reflux for 4 hours, the mixture was diluted with ethyl acetate and washed successively with water, 5% potassium bisulfate (twice), and brine, dried ($MgSO_4$) and evaporated. The residue (4.0 g.) was chromatographed on silica (130 g.) eluting with 1:1 toluene/acetone to give 2.6 g. (5.3 mmole) of 1-[[ethyl[[ethoxy-(2-phenylethyl)phosphinyl]methyl]amino]carbonyl]-L-proline, phenylmethyl ester as an oil. Tlc (5% methanol/dichloromethane) major spot at $R_f=0.5$.

(d) 1-[[Ethyl[[hydroxy(2-phenylethyl)phosphinyl]methyl]amino]carbonyl]-L-proline, phenylmethyl ester A mixture of 2.5 g. (5.1 mmole) 1-[[ethyl-[[ethoxy(2-phenylethyl)phosphinyl]methyl]amino]-carbonyl]-L-proline, phenylmethyl ester, dry dichloromethane (8 ml.) and trimethylsilylbromide (1.5 ml., 10 mmole) was stirred under argon at 25° for 3 hours. The dichloromethane and excess trimethylsilylbromide were removed in vacuo and the residue partitioned between ethyl acetate/water. The organic phase was washed with brine, dried ($MgSO_4$), and evaporated to give 2.3 g. (5.1 mmole) of 1-[[ethyl[[hydroxy(2-phenylethyl)phosphinyl]methyl]amino]carbonyl]-L-proline, phenylmethyl ester as an oil which crystallized on standing; m.p. 110°–111°. Tlc (isopropanol/con. $NH_4OH$/water, 7:2:1) single spot at $R_f=0.8$.

(e) 1-[[Ethyl[[hydroxy(2-phenylethyl)phosphinyl]methyl]amino]carbonyl]-L-proline, dilithium salt A mixture of 1-[[ethyl[[hydroxy(2-phenylethyl)phosphinyl]methyl]amino]carbonyl]-L-proline, phenylmethyl ester (1.15 g., 2.5 mmole), methanol (40 ml.), and 10% palladium on carbon catalyst (400 mg.) was hydrogenated in a Parr apparatus at 50 psi for 1.5 hours. The catalyst was removed by filtration through a Celite bed and the solvent evaporated. The residue was taken up in 1 N lithium hydroxide (5.1 ml., 5.1 mmole) and chromatographed on an HP-20 (220 ml. bed volume) column eluting with a linear gradient of water/acetonitrile (0→90%). The desired fractions were combined, evaporated to dryness, taken up in water, filtered (millipore), and lyophilized to give 690 mg. (1.8 mmole) of 1-[[ethyl[[hydroxy(2-phenylethyl)phosphinyl]methyl]-amino]carbonyl]-L-proline, dilithium salt as a dense white solid; m.p. 245° (dec.). Tlc (isopropanol/conc. $NH_4OH$/water, 7:2:1) single spot at $R_f=0.6$.

Anal. calc'd. for $C_{17}H_{23}N_2O_5PLi\cdot0.5\ H_2O$: C, 52.45; H, 6.21; N, 7.20; P, 7.9. Found: C, 52.71; H, 6.43; N, 7.07; P, 7.9.

EXAMPLES 50-56

Following the procedure of Examples 48 and 49 but employing the amine shown in Col. I and the phosphonite shown in Col. II one obtains the phosphinic acid shown in Col. III. Coupling of this intermediate with the acid chloride L-proline, phenylmethyl ester of Col. IV yields the products of Col. V. The $R_2$ and $R_4$ ester groups can then be removed to yield the corresponding diacid product.

Col. I $H_2N-R_1$

Col. II $R_3-P(OR_2)-OR_2$

Col. III

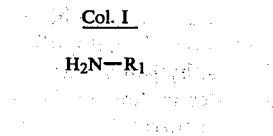

Col. IV

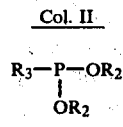

Col. V

| Example | $R_1$ | $R_2$ | $R_3$ |
|---|---|---|---|
| 50 | $H_3C-(CH_2)_3-$ | $-C_2H_5$ | $\text{C}_6\text{H}_5\text{-CH}_2-$ |
| 51 | $F_3C-CH_2-$ | $-C_2H_5$ | $\text{C}_6\text{H}_5-$ |
| 52 | $Cl_3C-CH_2-$ | $-C_2H_5$ | $Cl\text{-C}_6\text{H}_4\text{-}(CH_2)_4-$ |
| 53 | $\text{C}_6\text{H}_5\text{-CH}_2-$ | $-C_2H_5$ | thienyl-$CH_2-$ |
| 54 | $\text{C}_6\text{H}_5\text{-}(CH_2)_2-$ | $-C_2H_5$ | furyl-$(CH_2)_2-$ |
| 55 | phthalimido-$(CH_2)_4-$ | $-C_2H_5$ | $H_3C-(CH_2)_5-$ |
| 56 | phthalimido-$(CH_2)_2-$ | $-C_2H_5$ | $\text{C}_6\text{H}_5\text{-}(CH_2)_2-$ |

The $R_1$ phthalimido protecting group shown in Examples 55 and 56 is removed following completion of the coupling reaction by treatment with hydrazine.

The various imino acid esters shown in Col. II of Examples 2 to 47 could be employed in place of L-proline, phenylmethyl ester in the procedure of Examples 48-56 to yield other products within the scope of this invention.

EXAMPLE 57

1-[[Methyl[[hydroxy(4-phenylbutyl)phosphinyl]-methyl]amino]carbonyl]-L-proline, dilithium salt (a) 1-[[Methyl[[ethoxy(4-phenylbutyl)phosphinyl]-methyl]amino]carbonyl]-L-proline, phenylmethyl ester.

A solution of 1-[[[[ethoxy(4-phenylbutyl)-phosphinyl]methyl]amino]carbonyl]-L-proline, phenylmethyl ester (2.43 g., 5 mmole) in dry tetrahydrofuran (15 ml.) is treated with 50% sodium hydride oil dispersion (0.24 g., 5 mmole) and stirred at room temperature for one hour. The mixture is then treated with methyl iodide (0.34 ml., 5.5 mmole) and stirred at room temperature for an additional 3 hours. The mixture is then partitioned between ethyl acetate-5% potassium bisulfate. The organic phase is washed successively with saturated sodium bicarbonate and saturated sodium chloride, dried (Na₂SO₄) and evaporated. The residue is purified by flash chromatography on silica eluting with acetone/dichloromethane (2:3) to give 1-[[methyl[[ethoxy(4-phenylbutyl)phosphinyl]methyl]amino]carbonyl]-L-proline, phenylmethyl ester.

(b) 1-[[Methyl[[hydroxy(4-phenylbutyl)phosphinyl]methyl]amino]carbonyl]-L-proline, phenylmethyl ester A mixture of 1-[[methyl[[ethoxy(4-phenylbutyl)phosphinyl]methyl]amino]carbonyl]-L-proline, phenylmethyl ester, dry dichloromethane, and trimethylsilylbromide is stirred under argon at room temperature for several hours. The dichloromethane and excess trimethylsilylbromide are removed in vacuo and the residue is partitioned between ethyl acetate/water. The organic phase is washed with brine, dried, and evaporated to give 1-[[methyl[[hydroxy(4-phenylbutyl)phosphinyl]methyl]amino]carbonyl]-L-proline, phenylmethyl ester.

(c) 1-[[methyl[[hydroxy(4-phenylbutyl)phosphinyl]methyl]amino]carbonyl]-L-proline, dilithium salt A mixture of 1-[[methyl[[hydroxy(4-phenylbutyl)phosphinyl]methyl]amino]carbonyl]-L-proline, phenylmethyl ester, methanol, and 10% palladium on carbon catalyst is hydrogenated in a Parr apparatus at 50 psi for several hours. The catalyst is removed by filtration and the solvent evaporated. The residue is taken up in 1 N lithium hydroxide and chromatographed on an HP-20 column eluting with a linear gradient of water/acetonitrile (0→90%). The desired fractions are combined, evaporated to dryness, taken up in water, filtered, and lyophilized to give 1-[[methyl[[hydroxy(4-phenylbutyl)phosphinyl]methyl]amino]carbonyl]-L-proline, dilithium salt.

EXAMPLES 58–64

Following the procedure of Example 57 but substituting for the methyl iodide the reactant listed in Col. I the diester listed in Col. II is obtained. Removal of the R₂ and R₄ ester groups yields the corresponding diacid product.

Col. I

R₁—hal

Col. II

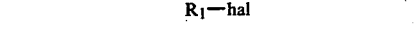

| Example | R₁—hal |
|---------|--------|
| 58 | ⟨phenyl⟩—CH₂—Br |
| 59 | ⟨phenyl⟩—(CH₂)₂—Br |
| 60 | (CH₃)₂CHCH₂—I |
| 61 | phthalimido-N—(CH₂)₃—Br |
| 62 | phthalimido-N—CH₂—Br |
| 63 | phthalimido-N—(CH₂)₄—Br |
| 64 | H₃C—(CH₂)₂—I |

In the case of Examples 61 to 63, the phthalimido protecting group would be removed as the last step of the synthesis.

Also, by substituting the diester compounds shown in Col. III of Examples 2 to 47 for the 1-[[[[ethoxy(4-phenylbutyl)phosphinyl]methyl]amino]carbonyl]-L-proline, phenylmethyl ester in the procedure of Examples 57 to 64 other compounds within the scope of the invention are obtained.

EXAMPLE 65

1-[[Ethyl[[[(2,2-dimethyl-1-oxopropoxy)methoxy](4-phenylbutyl)phosphinyl]methyl]amino]carbonyl]-L-proline (a) 1-[[Ethyl[[[(2,2-dimethyl-1-oxopropoxy)-methoxy](4-phenylbutyl)phosphinyl]methyl]amino]carbonyl]-L-proline, phenylmethyl ester An equimolar mixture of triethylamine and chloromethyl pivalate are added to a solution of 1-[[ethyl[[hydroxy(4-phenylbutyl)phosphinyl]methyl]amino]carbonyl]-L-proline, phenylmethyl ester in dimethylformamide under argon. The mixture is stirred for several hours at room temperature, diluted with ethyl acetate, washed with water, brine, dried (MgSO₄), and evaporated. The crude product is chromatographed to give 1-[[ethyl[[[(2,2-dimethyl-1-oxopropoxy) methoxy](4-phenylbutyl)phosphinyl]methyl]amino]carbonyl]-L-proline, phenylmethyl ester.

(b) 1-[[Ethyl[[[(2,2-dimethyl-1-oxopropoxy)methoxy](4-phenylbutyl)phosphinyl]methyl]amino]carbonyl]-L-proline A solution of the diester product from part (a) in methanol is added to a 10% palladium on carbon catalyst and the resulting mixture is shaken in a Parr hydrogenation apparatus for several hours. The catalyst is filtered off and the methanol is stripped from the filtrate. The crude product is chromatographed on silica gel to yield 1-[[ethyl[[[(2,2-dimethyl-1-oxopropoxy)methoxy](4-phenylbutyl)phosphinyl]methyl]amino]carbonyl]-L-proline.

EXAMPLES 66–70

Following the procedure of Example 65 but employing the alkylating agent shown in Col. I in place of the chloromethyl pivalate, one obtains the product listed in Col. II.

| Example | Col. I | Col. II |
|---|---|---|
| 66 | Br—CH₂—O—C(=O)—CH₃ | 1-[[ethyl[[[(acetyloxy)methoxy](4-phenylbutyl)phosphinyl]methyl]amino]carbonyl]-L-proline |
| 67 | Cl—CH(CH₃)—O—C(=O)—OC₂H₅ | 1-[[ethyl[[[1-(ethoxycarbonyloxy)ethoxy](4-phenylbutyl)phosphinyl]methyl]amino]carbonyl]-L-proline |
| 68 | (3-oxo-1-isobenzofuranyl bromide) | 1-[[ethyl[[(3-oxo-1-isobenzofuranyloxy)(4-phenylbutyl)phosphinyl]methyl]amino]carbonyl]-L-proline |
| 69 | ClCH₂—O—C(=O)—C₆H₅ | 1-[[ethyl[[[(benzoyloxy)methoxy]4-phenylbutyl)phosphinyl]methyl]amino]carbonyl]-L-proline |
| 70 | Cl—CH(CH(CH₃)₂)—O—C(=O)—C₂H₅ | 1-[[ethyl[[[2-methyl-1-(1-oxopropoxy)propoxy](4-phenylbutyl)phosphinyl]methyl]amino]carbonyl]-L-proline |

Similarly, the alkylating agents of Examples 65 to 70 can be employed with the compounds of Examples 1 to 47 and 49 to 64 to yield other compounds within the scope of this invention.

EXAMPLE 71

1-[[Ethyl[[hydroxy(4-phenylbutyl)phosphinyl]methyl]amino]carbonyl]-L-proline, disodium salt Following the procedure of Example 48 but substituting AG-50W-X8 (Na+) for the lithium resin in part (g), one obtains 1-[[ethyl[[hydroxy(4-phenylbutyl)phosphinyl]methyl]amino]carbonyl]L-proline, disodium salt.

This procedure can be employed in Examples 1 to 47 and 49 to 70 to give the corresponding mono or disodium salt. Similarly, by employing a potassium resin the corresponding mono or dipotassium salt is obtained.

EXAMPLE 72

1000 tablets each containing the following ingredients:

| | |
|---|---|
| 1-[[Ethyl[[hydroxy(4-phenylbutyl)phosphinyl]methyl]amino]carbonyl]-L-proline, disodium salt | 100 mg. |
| Corn starch | 50 mg. |
| Gelatin | 7.5 mg. |
| Avicel(microcrystalline cellulose) | 25 mg. |
| Magnesium stearate | 2.5 mg. |
| | 185 mg. | are prepared from sufficient bulk quantities by mixing the 1-[[ethyl[[hydroxy(4-phenylbutyl)phosphinyl]methyl]amino]carbonyl]-L-proline, disodium salt and corn starch with an aqueous solution of the gelatin. The mixture is dried and ground to a fine powder. The Avicel and then the magnesium stearate are admixed with granulation. This mixture is then compressed in a tablet press to form 1000 tablets each containing 100 mg. of active ingredient.

In a similar manner, tablets containing 100 mg. of the product of any of Examples 1 to 70 can be prepared.

EXAMPLE 73

1000 tablets each containing the following ingredients:

| | |
|---|---|
| 1-[[Ethyl[[[(2,2-dimethyl-1-oxopropoxy)methoxy](4-phenylbutyl)phosphinyl]methyl]amino]carbonyl]-L-proline, sodium salt | 50 mg. |
| Lactose | 25 mg. |
| Avicel | 38 mg. |
| Corn starch | 15 mg. |
| Magnesium stearate | 2 mg. |
| | 130 mg. | are prepared from sufficient bulk quantities by mixing the 1-[[ethyl[[[(2,2-dimethyl-1-oxopropoxy methoxy](4-phenylbutyl)phosphinyl]methyl]amino]-carbonyl]-L-proline, sodium salt, lactose and Avicel and then blending with the corn starch. Magnesium stearate is added and the dry mixture is compressed in a tablet press to form 1000 tablets each containing 50 mg. of active ingredient. The tablets are coated with a solution of Methocel E 15 (methyl cellulose) including as a color a lake containing yellow #6.

In a similar manner, tablets containing 50 mg. of the product of any Examples 1 to 64 and 66 to 71 can be prepared.

EXAMPLE 74

Two-piece #1 gelatin capsules each containing 100 mg. of 1-[[ethyl[[hydroxy(2-phenylethyl) phosphinyl]methyl]amino]carbonyl]-L-proline, disodium salt are filled with a mixture of the following ingredients:

| | |
|---|---|
| 1-[[Ethyl[[hydroxy(2-phenylethyl)phosphinyl]methyl]amino]carbonyl]-L-proline, disodium salt | 100 mg. |
| Magnesium stearate | 7 mg. |
| Lactose | 193 mg. |

-continued

| | 300 mg. |
|---|---|

In a similar manner, capsules containing 100 mg. of the product of any of Examples 1 to 48 and 50 to 71 can be prepared.

EXAMPLE 75

An injectable solution is prepared as follows:

| 1-[[[[Hydroxy(4-phenyl-butyl)phosphinyl]methyl]-amino]carbonyl]-L-proline, disodium salt | 500 g. |
|---|---|
| Methyl paraben | 5 g. |
| Propyl paraben | 1 g. |
| Sodium chloride | 25 g. |
| Water for injection | 5 l |

The active substance, preservatives, and sodium chloride are dissolved in 3 liters of water for injection and then the volume is brought up to 5 liters. The solution is filtered through a sterile filter and asceptically filled into presterilized vials which are closed with presterilized rubber closures. Each vial contains 5 ml. of solution in a concentration of 100 mg. of active ingredient per ml. of solution for injection.

In a similar manner, an injectable solution containing 100 mg. of active ingredient per ml. of solution can be prepared for the product of any Examples 2 to 71.

EXAMPLE 76

1000 tablets each containing the following ingredients:

| 1-[[Ethyl[[hydroxy(4-phenyl-butyl)phosphinyl]methyl]amino]-carbonyl]-L-proline, disodium salt | 100 mg. |
|---|---|
| Avicel | 100 mg. |
| Hydrochlorothiazide | 12.5 mg. |
| Lactose | 113 mg. |
| Corn starch | 17.5 mg. |
| Stearic acid | 7 mg. |
| | 350 mg | are prepared from sufficient bulk quantities by slugging the 1-[[ethyl[[hydroxy(4-phenylbutyl)phosphinyl]methyl]amino]carbonyl]-L-proline, disodium salt, Avicel and a portion of the stearic acid. The slugs are ground and passed through a #2 screen, then mixed with the hydrochlorothiazide, lactose, corn starch, and remainder of the stearic acid. The mixture is compressed into 350 mg. capsule shaped tablets in a tablet press. The tablets are scored for dividing in half.

In a similar manner, tablets can be prepared containing 100 mg. of the product of any of Examples 1 to 70.

What is claimed is:

1. A compound of the formula

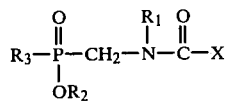

and a pharmaceutically acceptable salt thereof wherein:
X is an imino acid of the formula

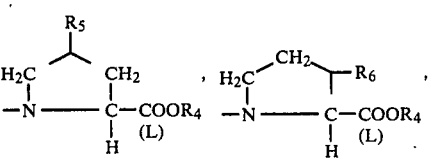

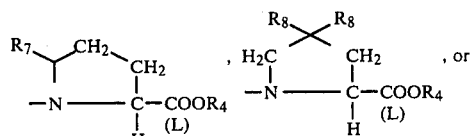

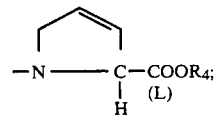

$R_5$ is hydrogen, lower alkyl, halogen, keto, hydroxy,

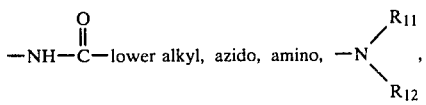

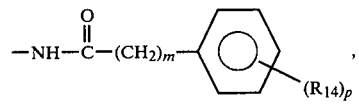

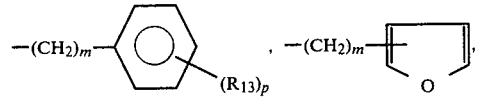

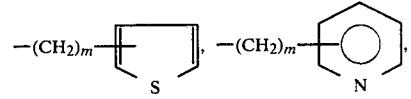

a 1- or 2-naphthyl of the formula

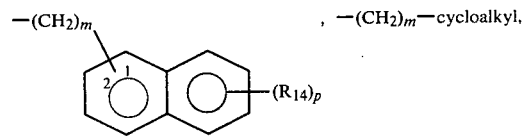

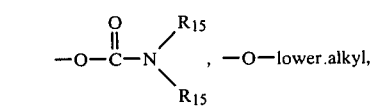

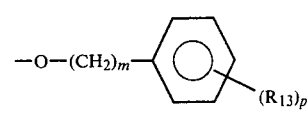

a 1- or 2-naphthyloxy of the formula

—O—(CH₂)ₘ— 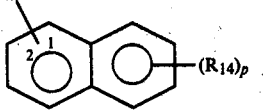 , —S—lower alkyl,

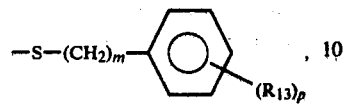

or a 1- or 2-naphthylthio of

—S—(CH₂)ₘ— 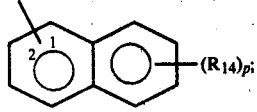;

R₆ is keto, halogen,

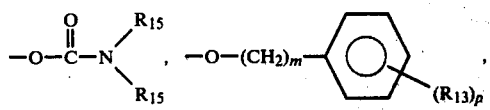

—O—lower alkyl, a 1- or

—O—(CH₂)ₘ— 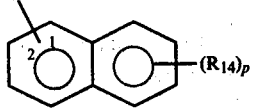 , —S—lower alkyl,

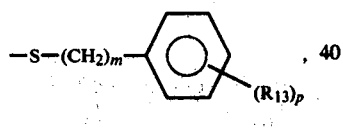

or a 1- or

—S—(CH₂)ₘ— 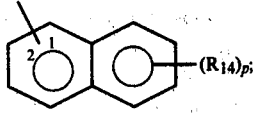;

R₇ is keto or

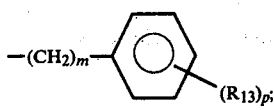;

R₈ is halogen or —Y—R₁₆;
R₁₁ is lower alkyl, benzyl, or phenethyl;
R₁₂ is hydrogen, lower alkyl, benzyl or phenethyl;
R₁₃ is hydrogen, lower alkyl or 1 to 4 carbons, lower alkoxy or 1 to 4 carbons, lower alkylthio of 1 to 4 carbons, chloro, bromo, fluoro, trifluoromethyl, hydroxy, phenyl, phenoxy, phenylthio, or benzyl;
R₁₄ is hydrogen, lower alkyl of 1 to 4 carbons, lower alkoxy of 1 to 4 carbons, lower alkylthio of 1 to 4 carbons, chloro, bromo, fluoro, trifluoromethyl, or hydroxy;
m is zero, one, two, three or four;
p is one, two or three provided that p is more than one only if R₁₃ or R₁₄ is hydrogen, methyl, methoxy, chloro, or fluoro;
R₁₅ is hydrogen or lower alkyl of 1 to 4 carbons;
Y is oxygen or sulfur;
R₁₆ is lower alkyl of 1 to 4 carbons, —(CH₂)ₘ— 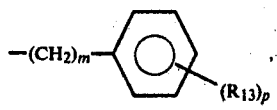, or the R₁₆ groups join to complete an unsubstituted 5- or 6-membered ring or said ring in which one or more of the carbons has a lower alkyl of 1 to 4 carbons or a di(lower alkyl of 1 to 4 carbons) substituent;
R₁ is hydrogen, lower alkyl, halo substituted lower alkyl, amino substituted lower alkyl, benzyl, or phenethyl;
R₂ and R₄ are independently selected from the group consisting of hydrogen, lower alkyl, benzyl, benzhydryl, and

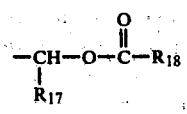

wherein R₁₇ is hydrogen, alkyl, cycloalkyl, or phenyl, and R₁₈ is hydrogen, alkyl, cycloalkyl, lower alkoxy, phenyl, benzyl, phenethyl, or R₁₇ and R₁₈ taken together are —(CH₂)₂—, —(CH₂)₃—, —CH=CH—, or

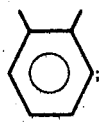;

and
R₃ is alkyl, halo substituted lower alkyl, amino substituted lower alkyl, cycloalkyl-(CH₂)ₙ-,

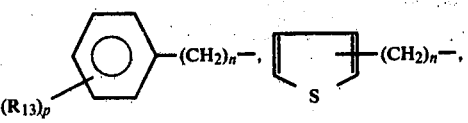

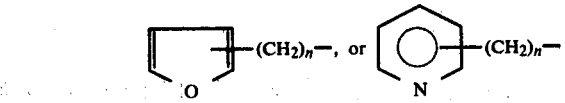

wherein R₁₃, m and p are as defined above and n is zero or an integer from 1 to 7.
2. A compound of claim 1 wherein:
R₅ is hydrogen, hydroxy, chloro, fluoro, lower alkyl of 1 to 4 carbons, cyclohexyl, amino, —O—lower alkyl wherein lower alkyl of of 1 to 4 carbons,

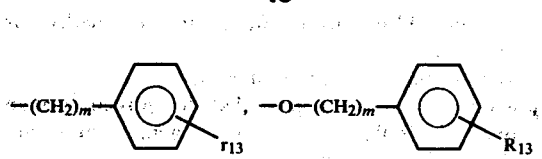

1- or 2-napthtyloxy, S-lower alkyl wherein lower alkyl is of 1 to 4 carbons,

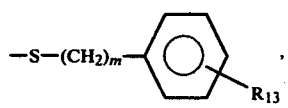

or 1- or 2-naphthylthio;
$R_6$ is —O—lower alkyl wherein lower alkyl is of 1 to 4 carbons, —S—lower alkyl wherein lower alkyl is 1 to 4 carbons,

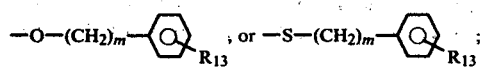

$R_7$ is phenyl, 2-hydroxyphenyl, or 4-hydroxyphenyl;
$R_8$ are both fluoro, both chloro, or —Y—$R_{16}$;
Y is oxygen or sulfur;
$R_{16}$ is lower alkyl of 1 to 4 carbons or the $R_{16}$ groups join to complete an unsubstituted 5- or 6-membered ring or said ring in which one or more of the carbons has a methyl or dimethyl substituent;
m is zero, one or two;
$R_{13}$ is hydrogen, methyl, methoxy, methylthio, chloro, bromo, fluoro, or hydroxy;
$R_1$ is hydrogen, lower alkyl of 1 to 4 carbons, or amino substituted lower alkyl of 1 to 4 carbons;
$R_2$ and $R_4$ are independently selected from hydrogen, alkali metal salt, lower alkyl of 1 to 4 carbons, or $$-\underset{\underset{R_{17}}{|}}{CH}-O-\overset{O}{\underset{||}{C}}-R_{18};$$

$R_{17}$ is hydrogen, straight or branched chain lower alkyl of 1 to 4 carbons, or cyclohexyl;
$R_{18}$ is straight or branched chain lower alkyl of 1 to 4 carbons or phenyl; and
$R_3$ is alkyl of 1 to 10 carbons,

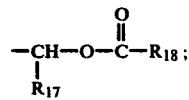

cycloalkyl-$(CH_2)_n$- wherein cycloalkyl is of 5 or 6 carbons, amino substituted lower alkyl,

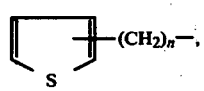

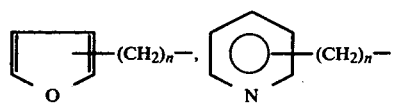

wherein $R_{13}$ and m are as defined above and n is zero or an integer from 1 to 4.

3. A compound of claim 2 wherein X is

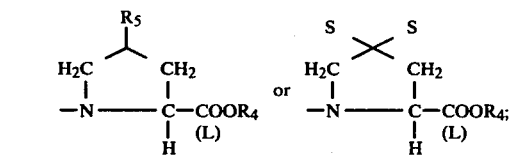

$R_5$ is hydrogen, cyclohexyl, lower alkoxy of 1 to 4 carbons,

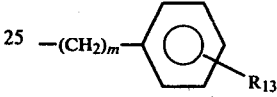

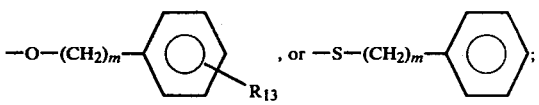

m is zero, one or two;
$R_{13}$ is hydrogen, mehthyl, methoxy, methylthio, bromo, fluoro, or hydroxy;
t is two or three; and
$R_4$ is hydrogen, $$-\underset{\underset{CH_3}{|}}{CH}-O-\overset{O}{\underset{||}{C}}-CH_3, \quad -\underset{\underset{\underset{(CH_3)_2}{|}}{CH}}{CH}-O-\overset{O}{\underset{||}{C}}-C_2H_5,$$

$$-\underset{\underset{CH_3}{|}}{CH}-O-\overset{O}{\underset{||}{C}}-C_2H_5, \quad -CH_2-O-\overset{O}{\underset{||}{C}}-C(CH_3)_3,$$

or an alkali metal salt.
4. A compound of claim 3 wherein $R_3$ is alkyl of 1 to 10 carbons.
5. A compound of claim 3 wherein $R_3$ is amino substituted lower alkyl.
6. A compound of claim 3 wherein $R_3$ is

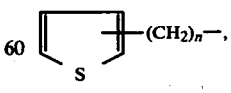

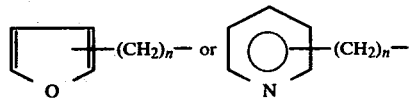

and n is zero or an integer from 1 to 4.

7. A compound of claim 3 wherein $R_3$ is

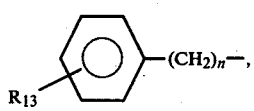

$R_{13}$ is hydrogen, methyl, methoxy, methylthio, chloro, bromo, fluoro, or hydroxy, and n is zero or an integer from 1 to 4.

8. A compound of claim 7 wherein X is

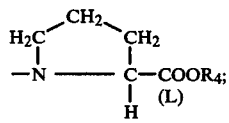

$R_1$ is hydrogen; $R_3$ is

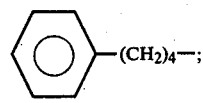

and $R_2$ and $R_4$ are the same and each is hydrogen, sodium, potassium, or lithium.

9. The compound of claim 8, 1-[[[[hydroxy(4-phenylbutyl)phosphinyl]methyl]amino]carbonyl]-L-proline, dilithium salt.

10. A compound of claim 7 wherein X is

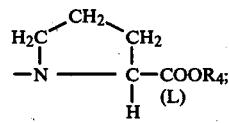

$R_1$ is $-C_2H_5$; $R_3$ is

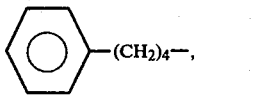

and $R_2$ and $R_4$ are the same and each is hydrogen, sodium, potassium, or lithium.

11. The compound of claim 10, 1-[[ethyl[[hydroxy(4-phenylbutyl)phosphinyl]methyl]amino]carbonyl]-L-proline.

12. A compound of claim 7 wherein X is

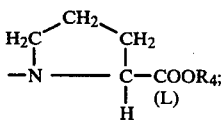

$R_1$ is $-C_2H_5$; $R_3$ is

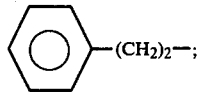

$R_2$ and $R_4$ are the same and each is hydrogen, sodium, potassium or lithium.

13. The compound of claim 12 1-[[ethyl[[hydroxy(2-phenylethyl)phosphinyl]methyl]amino]carbonyl]-L-proline, dilithium salt.

14. A composition useful for treating hypertension comprising a pharmaceutically acceptable carrier and a hypotensive agent or pharmaceutically acceptable salt thereof of the formula

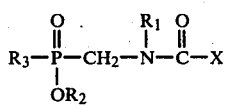

wherein $R_1$, $R_2$, $R_3$ and X are as defined in claim 1.

15. The method of alleviating hypertension in a mammalian species which comprise administering an effective amount of the composition of claim 14.

* * * * *

UNITED STATES PATENT AND TRADEMARK OFFICE
CERTIFICATE OF CORRECTION

PATENT NO. : 4,448,772
DATED : May 15, 1984
INVENTOR(S) : Donald S. Karanewsky

It is certified that error appears in the above-identified patent and that said Letters Patent are hereby corrected as shown below:

Column 3, line 5, second formula should read

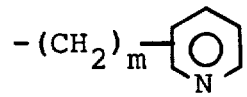

Column 12, line 55, the top portion of the second formula should read

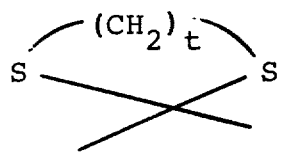

UNITED STATES PATENT AND TRADEMARK OFFICE
CERTIFICATE OF CORRECTION

PATENT NO. : 4,448,772
DATED : May 15, 1984
INVENTOR(S) : Donald S. Karanewsky

It is certified that error appears in the above-identified patent and that said Letters Patent are hereby corrected as shown below:

Column 41, line 14, after of should be inserted -- the formula--
Column 41, line 30 after or should be inserted --
2-naphthyloxy of the formula --.
Column 41, line 44, after or should be inserted --
2-naphthylthio of the formula --.
Column 44, line 13, the top portion of the secon formula should read

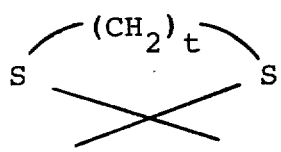

Signed and Sealed this

Fourth Day of February 1986

[SEAL]

Attest:

DONALD J. QUIGG

Attesting Officer

Commissioner of Patents and Trademarks